United States Patent [19]

Odstrchel et al.

[11] Patent Number: 5,366,870
[45] Date of Patent: Nov. 22, 1994

[54] LIMITED ENZYME ASSAY FOR AMINOTRANSFERASES

[75] Inventors: Gerald Odstrchel, San Juan Capistrano; George Leung, San Diego, both of Calif.

[73] Assignee: Xytronyx, Inc., San Diego, Calif.

[21] Appl. No.: 42,417

[22] Filed: Apr. 2, 1993

[51] Int. Cl.$^5$ .................. C12Q 1/52; C12Q 1/34; G01N 21/00
[52] U.S. Cl. ........................ 435/16; 435/18; 435/24; 435/808; 435/810; 422/58
[58] Field of Search ............ 435/16, 18, 24, 808, 435/810; 422/58

[56] References Cited

U.S. PATENT DOCUMENTS

| | | | |
|---|---|---|---|
| 3,875,014 | 4/1975 | Forgione | 195/103.5 R |
| 4,241,179 | 12/1980 | Madappally | 435/16 |
| 4,801,535 | 1/1989 | Babler | 435/16 |
| 4,897,347 | 1/1990 | Katsuyama | 435/16 |
| 4,923,800 | 5/1990 | Ly | 435/10 |
| 4,981,787 | 1/1991 | Baram | 435/16 |
| 5,047,328 | 9/1991 | Chambers | 435/16 |

FOREIGN PATENT DOCUMENTS 9213966  8/1992  WIPO.

*Primary Examiner*—Michael G. Wityshyn
*Assistant Examiner*—Ralph Gitomer
*Attorney, Agent, or Firm*—Lyon & Lyon

[57] ABSTRACT

Method for determining the presence of an aminotransferase ($AT_1$), other than aspartate aminotransferase (AST), in a biological sample. The method includes contacting the sample with an amino donor substrate for $AT_1$, an amino acceptor substrate for $AT_1$, cysteine sulfinic acid (CSA) in excess, a second aminotransferase ($AT_2$), different from $AT_1$, in excess, and an indicator for the presence of sulfite ions, under conditions in which the concentration of said $AT_1$ can be determined by the amount of the indicator which forms a detectable signal.

28 Claims, No Drawings

LIMITED ENZYME ASSAY FOR AMINOTRANSFERASES

BACKGROUND OF THE INVENTION

The invention relates to methods and assay kits for identifying aminotransferases, other than aspartate aminotransferase (AST), in biological samples.

Baram, U.S. Pat. No. 4,981,787 disclosed a method for diagnosing periodontal disease by detection of L-alanine aminotransferase activity. Specifically, a colorimetric assay with diazo dyes is used to determine ALT activity.

Maupin, PCT/US92/00865 discusses a method determining AST levels by reaction of AST with the substrate cysteine sulfinic acid (CSA) in the presence of a sulfite-reactive dye compound, such as triarylmethine dye.

SUMMARY OF THE INVENTION

This invention features a convenient assay method for the detection of aminotransferases, such as L-alanine aminotransferase (ALT). In the method, an excess of a second aminotransferase ($AT_2$), different from the aminotransferase to be detected ($AT_1$), is used combination with excess cysteine sulfinic acid, an appropriate amino donor substrate for the aminotransferase ($AT_1$), and an appropriate amino acceptor substrate for the aminotransferase ($AT_1$). Dyes such as those of the triarylmethine family, with or without contrast dyes, allow for the detection of the aminotransferase ($AT_1$).

The method of the invention is more versatile, and more sensitive than other assay schemes for aminotransferases. The assay method can be adopted for the detection of a wide range of aminotransferases. The triarylmethine dyes of the current invention have a higher extinction coefficient and thus a greater sensitivity (greater optical density change per concentration of dye) than the diazo dyes used in other methods.

The following is the general scheme for the assay method of the invention. In this scheme, an amino donor and an amino acceptor are reacted with an aminotransferase ($AT_1$) present in a sample, to provide a $\beta$-keto acid in an amount proportional to the amount of $AT_1$ present in the sample. The $\beta$-keto acid is then reacted with excess cysteine sulfinic acid in the presence of an excess of a second aminotransferase ($AT_2$), different from $AT_1$, to provide $\beta$-sulfinyl acid. The $\beta$-sulfinyl acid is unstable and converted spontaneously to sulfite ions. The sulfite ions can then react with an indicator to form a detectable signal. The amount of $AT_1$ in the sample level can be determined by measuring the detectable signal.

In a first aspect, the invention features a method for determining the presence of an aminotransferase ($AT_1$), other than aspartate aminotransferase (AST), in a biological sample. The method includes contacting the sample with an amino donor substrate for $AT_1$; a second aminotransferase ($AT_2$), different from $AT_1$, in excess; an amino acceptor substrate for $AT_1$, nonreactive with $AT_2$; cysteine sulfinic acid (CSA) in excess; and an indicator for the presence of sulfite ions, nonreactive with $AT_1$, $AT_2$, CSA, the amino donor substrate, and the amino acceptor substrate; under conditions in which the concentration of $AT_1$ can be determined by the amount of indicator which forms a detectable signal.

By "aminotransferase" is meant an enzyme, such as alanine aminotransferase (ALT), glycine aminotransferase, tyrosine aminotransferase, leucine aminotransferase, etc., which catalyzes the transfer of an amino group from an $\alpha$-amino acid to an $\alpha$-keto acid. In the process, a new amino acid and keto acid are formed.

By "amino donor substrate" is meant a substrate, such as an $\alpha$-amino acid, which provides an amino group for transferral to an amino acceptor in the reaction catalyzed by an aminotransferase and thus becomes a $\beta$-keto acid. For example, glutamate donates an amino group and becomes $\alpha$-ketoglutarate. The $\alpha$-amino acid may be a naturally occurring amino acid or a synthetic analog. The preferred range of the amino donor substrate concentration for this assay is variable, but will typically range from 1 mM to about 500 mM.

By "amino acceptor substrate" is meant a substrate, such as an $\alpha$-keto acid, which accepts an amino group from an amino donor substrate in the reaction catalyzed by an aminotransferase. For example, pyruvate accepts an amino group and becomes alanine. Preferably, the amino acceptor substrate should be nonreactive with the second aminotransferase ($AT_2$). However, if the amino acid acceptor can be utilized in both the reaction catalyzed by $AT_1$ and the reaction catalyzed by $AT_2$, then the rate of the reaction catalyzed by $AT_1$ should be from 5 to 1000 times greater than the rate of the reaction catalyzed by $AT_2$ when the amino acid acceptor is used. The preferred range of the amino acceptor substrate concentration for this assay is variable, but will typically range from 1 mM to about 500 mM.

By "second aminotransferase ($AT_2$)" is meant a aminotransferase different than the aminotransferase ($AT_1$) being detected in the sample. Preferably, the second aminotransferase uses cysteine sulfinic acid (CSA) as the amino donor substrate and the $\beta$-keto acid generated by the reaction catalyzed bt $AT_1$, as the amino acceptor substrate. However, if the amino acceptor substrate utilized by $AT_1$ can also be utilized by $AT_2$, then the reaction catalyzed by $AT_1$ should proceed at a rate 5 to 1000 times greater than the rate of the reaction catalyzed by $AT_2$ in which the amino donor substrate is used.

By "excess $AT_2$" is meant a level of $AT_2$ at which $AT_2$ will not limit the rate at which the $\beta$-keto acid, generated by the reaction catalyzed by $AT_1$, will be utilized. The appropriate amount of $AT_2$ will vary depending on the amount of $\beta$-keto acid generated by the reaction catalyzed by $AT_1$.

By "excess cysteine sulfinic acid (CSA)" is meant a level of CSA at which CSA will not become a rate limiting determinant in the enzymatic reaction catalyzed by $AT_2$.

By "indicator for the presence of sulfite ions" is meant a substance capable of reacting with sulfite ions to produce a detectable signal. The change in the indicator is proportional to the quantity of sulfite ions generated in the assay. The indicator is nonreactive with $AT_1$, $AT_2$, the amino donor substrate, the amino acceptor substrate, CSA, and the $\beta$-keto acid produced. A preferred aspect of the invention involves use of an indicator that undergoes a spectral change when it reacts with sulfite ions. Alternative embodiments of the invention employ indicators that respond to the presence of sulfite ion by forming a precipitate, producing a fluorescent or chemiluminescent signal, causing a change in the pH or ionic strength of a solution, producing an electrical signal by reaction with an electrode, and other such physical or chemical changes.

By "detectable signal" is meant a change in the indicator that can be measured using an instrument or is apparent visually. Methods for detecting a signal are readily apparent to the skilled practitioner. The level of the detectable signal can be used to determine the concentration of $AT_1$ in the sample.

By "biological sample" is meant a sample obtained from a living or non-living organism, animal or plant, or a portion thereof, which is thought to contain an aminotransferase. If the sample consists of a body tissue, it may be obtained from solid tissue or a body fluid, either endocrine or exocrine. Body fluid samples include: urine, plasma, sera, saliva, or fluid withdrawn from a particular organ,(e.g., cerebrospinal fluid, crevicular fluid), interstitial fluid, or inflammatory exudate.

In preferred embodiments, the aminotransferase is L-alanine aminotransferase (ALT); the indicator exhibits a detectable spectral change during the reaction; the indicator is a triarylmethine dye; the indicator contains a contrast dye; the aminotransferase reaction conditions include a buffered aqueous medium having pH in the range of about 3.0 to 10.0; the presence of the aminotransferase is indicative of a disease condition; the disease is periodontal disease; and the sample comprises crevicular fluid.

The enzyme L-alanine aminotransferase (E.C. 2.6.1.2) (ALT) is an intracellular enzyme widely distributed among mammalian tissues. Following acute tissue injury in the course of disease, trauma or toxicity, damaged cells release ALT into the circulation, interstitial fluid, inflammatory exudate and other bodily fluids. Elevated ALT in humans is indicative of tissue injury, most often associated with liver disease.

By "detectable spectral change" is meant a change in the absorbance or reflectance of the indicator upon reaction with sulfite ions, such change is detectable either by use of an instrument (e.g., spectrophotometer, reflectometer, fluorimeter, luminometer) or visually as a colorimetric change.

Indicators that result in a detectable spectral change are dyes. Suitable indicator dyes include di- and triarylmethine compounds, as well as aza, thia, or oxo analogs of the di- and triarylmethine dyes, polyene and polymethine dyes, aza[18]annulenes, nitro and nitroso dyes, azo dyes, carbonyl dyes, and sulphur dyes. Particularly preferred indicators are member of the triarylmethine family of dyes, which include malachite green, methyl green, guinea green, and salts thereof. A preferred concentration of the indicator is about 0.001–0.05% w/v.

By "contrast dye" is meant a dye, which enhances the visual detection of the spectral change of the indicator dye. If there is a loss of color when the indicator dye reacts with sulfite ions, the presence of the contrast dye facilitates detection of this change. The contrast dye is chemically inert and does not interfere with and is unaffected by sulfite ions or any other reagents used in the assay. The contrast dye is selected from the group consisting of rhodamine B, ethyl violet, acid fuchsin, basic fuchsin, pararosaniline chloride, pararosaniline acetate, aurin sodium salt and additional salts thereof. Preferred concentrations of the contrast dye are from 0.01 to about 1% w/v.

The detectable spectral change can be measured with an instrument. For example, if the indicator is malachite green, absorbance at 617 nm is extinguished upon reaction with sulfite ions, and this spectral change can be monitored by using a spectrophotometer. Visible detection of the spectral change is also possible, and is aided by the use of a contrast dye. The change in malachite green from green to colorless upon reaction with sulfite ions is made easier to visualize by a contrast dye, such as rhodamine B, which is pink in color.

By "buffered aqueous medium" is meant an aqueous medium that maintains a pH range in which the aminotransferases ($AT_1$ & $AT_2$) are stable and are able to catalyze their respective transferase reactions. The pH range is generally from 3.0 to 10.0. Buffers that are useful to maintain this pH range are Tris buffers at concentrations of 100 mM to 200 mM.

By "disease condition" is meant a condition resulting in an increase in the level of an aminotransferase. This could be the result of tissue injury in the course of disease (e,g., heart, liver or supportive tissue of the teeth (periodontal disease)), or the result of trauma or toxicity.

By "periodontal disease" is meant inflammatory diseases of microbial etiology affecting the supporting tissues of the teeth. The two major classes of periodontal disease are gingivitis and periodontitis. Gingivitis is characterized by inflammation of the gums in the absence of bone and attachment loss. Periodontitis is an advanced stage of gingivitis. Severe cases of periodontitis are associated with the loss of bone from the tooth and weakening of tooth attachment, eventually leading to tooth loss.

"Crevicular fluid" is a transudate of serum at the junction of the teeth and gums, and is characteristic of gingivitis and periodontitis.

In a second aspect, the invention features an assay kit for determining the presence of an aminotransferase ($AT_1$), other than aspartate aminotransferase (AST), in a biological sample. The kit comprises an enclosure of at least three containers comprising one or more of the following components: an aliquot of an amino donor substrate for $AT_1$; an aliquot of a second aminotransferase ($AT_2$), different from $AT_1$; an aliquot of cysteine sulfinic acid (CSA); an aliquot of an amino acceptor substrate for $AT_1$, nonreactive with $AT_2$; and an aliquot of an indicator for the presence of sulfite ion nonreactive with $AT_1$, $AT_2$, CSA, the amino acceptor substrate, and the amino donor substrate.

In preferred embodiments, the aminotransferase is L-alanine aminotransferase (ALT) and the biological sample is crevicular fluid; the amino donor is glutamate and the amino acceptor is pyruvate; the second aminotransferase ($AT_2$) is aspartate aminotransferase (AST); the assay kit contains a multiwell tray; the assay kit includes crevicular sampling papers; the indicator is a triarylmethine dye; the triarylmethine dye is selected from the group consisting of malachite green, methyl green, guinea green B, and additional salts thereof; a contrast dye is included with the indicator dye; the contrast dye is selected from the group consisting of rhodamine B, ethyl violet, acid fuchsin, basic fuchsin, pararosaniline chloride, pararosaniline acetate, aurin sodium salt and additional salts thereof; the amino donor substrate and the AST are provided in separate containers or are provided in the same container; and aliquots of the indicator dye, contrast dye and cysteine sulfinic acid (CSA) are coated onto wells of a multiwell tray, or coated onto paper, or provided in a sugar-based pellet, or provided in a powder form.

A "multiwell tray" consist of a series of wells made from conventional plastic materials, in which the assay reactions can be carried out. Each well is of sufficient volume to hold all the components necessary to conduct one test reaction.

"Crevicular fluid sampling papers" are strips of paper used to collect crevicular fluid by capillary action.

DESCRIPTION OF THE PREFERRED EMBODIMENTS

The following description and examples illustrate the method of the invention as used to detect L-alanine aminotransferases (ALT). Those in the art will recognize that these are not limiting to this invention.

In this scheme, an amino donor (glutamate) and an amino acceptor (pyruvate) are reacted with the ALT present in a sample to provide the products 2-oxoglutarate and alanine. The 2-oxoglutarate is then reacted with excess cysteine sulfinic acid in the presence of excess of aspartate aminotransferase (AST) to provide $\beta$-sulfinylpyruvate and glutamate. The $\beta$-sulfinylpyruvate is then converted spontaneously to pyruvate and sulfite ions. The sulfite ions react with an indicator, such as the triarylmethine dye malachite green, resulting in an extinction of absorbance at 617 nm and a change in color from green to colorless. The change in absorbance can be detected instrumentally and used to quantitate the amount of the ALT present in the sample (4a). Alternatively, the assay can be used in a semi-quantitative manner and the spectral change in the indicator can be detected visually. The use of a contrast dye results in a pink colored product when the malachite green changes from green to colorless, thus indicating the presence of ALT in the sample (4b).

The chemical reactions are as follows:

1. Glutamate + Pyruvate $\xrightarrow{ALT}$ 2-oxoglutarate + Alanine 2. 2-oxoglutarate + Cysteine sulfinate $\xrightarrow{AST}$ $\beta$-sulfinylpyruvate + Glutamate 3. $\beta$-sulfinylpyruvate $\longrightarrow$ Pyruvate + $SO_3^{2-}$ 4(a). $SO_3^{2-}$ + Indicator (Green) $\longrightarrow$ Reaction Product (Colorless)

4(b). $SO_3^{2-}$ + Indicator + Contrast Dye (Blue) $\longrightarrow$ Reaction Product (Pink)

EXAMPLE 1

Solutions for the Semi-Quantitative Assay Kits

Systems One (Three Bottle System)

Reconstitution Buffer
Tris base 100 mM
Glutamate 300 mM
EDTA 5 mM
PVP 1%
PP 0.0074%
TX-100 0.005%
AST 1500 U/L Dissolve 12.11 gm of Tris base, 50.72 gm of glutamic acid sodium salt, 1.86 gm of ethylenediaminetetraacetate (EDTA), 1.86 gm of polyvinyl pyrrolidone (PVP), 7.4 mg of pyridoxal phosphate (PP), and 50 mg of TRITON X-100 detergent (TX-100) in 1 liter of deionized water. Adjust the pH to 9.0. Add 1500 U of aspartate transaminase (AST) and mix well.

ALT Positive Control
Tris HCL 50 mM
Pyruvate 2 mM
BSA 0.5%
DTT 0.001%
PP 0.00074%
TX-100 0.005%
ALT 38 U/L Dissolve 7.88 gm of Tris HCl, 0.22 gm of pyruvic acid sodium salt, 5.0 gm of bovine serum albumin (BSA), 0.019 gm of dithiothreitol (DTT), 7.4 mg of pyridoxal phosphate (PP), and 50 mg of TRITON X-100 detergent (TX-100) in 1 liter of deionized water. Adjust pH to 5.5. Add 38 U of alanine transaminase (ALT) and mix well.

Starter Solution
Pyruvate 30 mM

Dissolve 3.3 gm of pyruvate acid sodium salt in 1 liter of deionized water.

System Two (Four Bottle System)

Reconstitution Buffer
Tris base 200 mM
Glutamate 50 mM
EDTA 5 mM

Dissolve 24.23 gm of Tris base, 8.47 gm of glutamic acid sodium salt, and 1.86 gm of ethylenediaminetetraacetate (EDTA) in 1 liter of deionized water. Adjust pH to 9.0.

AST Solution
Tris HCL 50 mM
Oxalacetate 1 mM
PP 0.03 mM
BSA 0.5%
AST 2400 U/L

Dissolve 7.88 gm of Tris HCL, 0.13 gm of oxalacetic acid, 7.4 mg of pyridoxal phosphate (PP), and 5.00 gm of bovine serum albumin (BSA) in 1 liter of deionized water. Adjust pH to 5.5. Add 2400 U of aspartate transaminase (AST) and mix well.

ALT Positive Control
Same as in System One.

Starter Solution
Same as in System One.

EXAMPLE 2

Preparation of Multiwells Coated with Indicator Dye, Contrast Dye, and CSA

Dye Stock Solution
Polyvinyl alcohol 3.5%
Malachite green
carbinol 0.14%
Rhodamine B 0.10%
Zinc chloride 0.06%
Manganese chloride 0.42 mM
TX-100 0.027%
Benzalkonium chloride 0.0004%

Solution A 10% Polyvinyl Alcohol Stock Solution

Dissolve 10 gm of polyvinyl alcohol (98% hydrolysis, 31K–50K) in 100 ml of deionized water at 80° C. with stirring. To this solution add 60 mg of TRITON X-100 detergent (TX-100), 1 mg of benzalkonium chloride and 4.2 gm of a 100 mM solution of manganese chloride. Mix well.

Solution B 3.5% Malachite Green Carbinol Stock Solution

Dissolve 3.5 gm of malachite green carbinol base in 100 ml of deionized water which contains 0.91% of zinc chloride (prepared from a 10% zinc chloride solution) and 0.1M HCL.

Solution C 1% Rhodamine B Solution

Dissolve 1 gm of Rhodamine B in 100 ml of deionized water which contains 0.06% of TRITON X-100 detergent (TX-100).

Preparation of Dye Stock Solution

To prepare 100 ml of the Dye Stock Solution: combine 35 ml of solution A, 4 ml of solution B, and 10 ml of solution C. Add 51 ml of deionized water.

Substrate Solution
Cysteine Sulfinic Acid 50 mM
EDTA 5 mM
TX-100 0.06%

To prepare 100 ml of the substrate solution: dissolve 0.765 gm of cysteine sulfinic acid in 100 ml of deionized water. Add 0.186 gm of ethylenediaminetetraacetate (EDTA) and 60 mg of TRITON X-100 detergent (TX-100). Mix well.

Procedure For Coating Multiwells

Mix dye stock solution and substrate solution at the ratio of 1 to 18, to produce coating solution. Coat each well with 100 ul of the coating solution. Let dry at room temperature in a ventilated area.

EXAMPLE 3

Preparation of Coated Paper Containing Indicator Dye, Contrast Dye, and CSA

Impregnate Whatman paper (Grade 4 CHR, Whatman) with the coating solution (as in Example 2) by slowly submerging the paper through the coating solution. Excess solution is gently squeezed out and the paper is hung to dry.

EXAMPLE 4

Preparation of Pellets Containing Indicator Dye, Contrast Dye, and CSA

CSA Solution
CSA 50 mM

Dissolve 0.38 gm of cysteine sulfinic acid in 4 ml of deionized water.

Dye Stock Solution
Same as in Example 2.

To CSA Solution add 5.8 ml of Dye Stock Solution and mix well. Add 20 gm of lactose. Dry the lactose slur under vacuum at 55° C. Mix the lactose-active ingredients powder with 1 to 2% of lubricants (e.g., myverol, leucine, or isoleucine) and 10 to 20% of microcrystalline cellulose. Prepare pellets with a pelleting machine.

EXAMPLE 5

Preparation of Powders Containing Indicator Dye, Contrast Dye, and CSA

Prepare as in Example 4, except do not add pill lubricants. Powders are reconstituted using the Reconstitution Buffer (System One or System Two).

EXAMPLE 6

System One Semi-Quantitative Assay Kit

The test involves collecting gingival crevicular fluid (GCF) samples from periodontal sites by means of sampling paper strips, and then performing a simple enzymatic test. The presence of ALT activity is indicated by a colorimetric reaction. In the absence of ALT and periodontal tissue destruction, the test solution remains blue. When elevated levels of ALT are present, the test solution turns pink. When low levels of ALT are present, the test solution turns purple/pink.

The multiwell test trays contain the CSA and indicator reagents necessary (indicator and contrast dyes) for running the colorimetric reaction. The dry ingredients are reconstituted by adding the Reconstitution Buffer, which also contains glutamate and AST. After test samples are collected the reaction is started by adding the Starter Solution, which contains the pyruvate. A positive control solution, containing a known amount of ALT, is supplied in another dispenser bottle, and is run simultaneously with the test samples. The test reaction is timed, and then the samples are scored by making visual comparison with the positive control. Those reactions with equal to or pinker in color than the positive control reaction are scored positive; reactions which are darker in color than the positive control (violet to blue) are scored negative.

The test procedure is as follows. The test must be performed before the prophylaxis (e.g., drug treatment) and before probing the gingival sulcus, so that cells are not disrupted and liberate additional ALT.

1. Select the periodontal sites to be tested. Label the wells in the kit tray to correspond to the selected test sites.

2. Prepare the test tray by adding three drops (100 ul) of Reconstitution Buffer to each test well and the two positive control wells. Mix by gently agitating the test tray for 20 seconds until there is complete dissolution.

3. Using forced air or gentle application of cotton, carefully dry each test site. Remove the unit of paper strips (Perio Test, Inc.) from the envelope. Using forceps remove a sampling paper from its holder and gently place in the gingival sulcus. Hold the paper in place for 10 seconds. Place the sampling paper containing the GCF sample in the corresponding test well. Repeat the drying and sampling steps for the other test sites.

4. After all of the test sites have been sampled, prepare the two positive control wells by adding one drop (30 ul) from the Positive Control Dispenser to each of the two center wells in the test tray.

5. Start the reaction by adding one drop (40 ul) of the Starter Solution to each test well and the two control wells and mix by gently agitating the test tray for 10 seconds.

6. Score the test when the positive control turns pink. The reaction time will vary depending on the room temperature. At temperatures lower than 20° C., score the test between 15 and 20 minutes; at temperatures higher than 25° C., score the test between 10 and 15 minutes. Obtain test results by comparing the color of each well to the color of the positive controls. If the color is equal to or pinker than the positive controls, the result is positive. If the color is darker (more violet) than the positive controls, the result is negative.

7. Appropriate treatment should be initiated. Treatment efficacy can be monitored with the test kit in 2–4 weeks. A decrease in ALT activity, as demonstrated by darker test results, is an indication of improvement.

EXAMPLE 7

System Two Semi-Quantitative Assay Kit

The procedure is the same as in system one, except that the glutamate and the AST are provided in separate solutions. The Reconstitution Buffer contains glutamate, and the AST Solution contains the AST. In step 2 of the protocol, two drops of Reconstitution Buffer (80 ul) and one drop of AST Solution (30 ul) are added to each well.

EXAMPLE 8

Other Semi-Quantitative Assay Kits

The semi-quantitative assay can also be performed in multiwells which are not coated with the indicator dye, contrast dye, and CSA or any other suitable reaction vessel. The assay procedure would be the same as in Examples 6 or 7, with the following modification in step 2. The indicator dye, contrast dye, and CSA would be added to the reactions via coated paper, as a sugar-based pill, or in powder form.

EXAMPLE 9

Quantitative Assay Method

The quantitative assay method differs from the semi-quantitative assay methods in that an instrument is used to quantitate the signal, the assay is performed in a vessel suitable for use with such an instrument (e.g., transparent microwells, microcuvettes), and a panel of standards consisting of various activity levels of the aminotransferase ($AT_1$) are also assayed so as to produce a standard curve. The assay components may be provided in any of the variations used for the semi-quantitative assays. The change in the indicator is dependant on the activity of the aminotransferase in the sample, which can be determined by the use of the standard curve.

The following example uses ALT as the aminotransferase to be measured, malachite green as the indicator, and is performed in microcuvettes.

Reaction Cocktail A
Tris buffer 100 mM
Glutamic acid 50 mM
CSA 50 mM
Pyruvic acid 8 mM
AST 1500 U/L Dissolve 12.11 gm of Tris base, 7.35 gm of glutamic acid, 7.6 gm of cysteine sulfinic acid (CSA), and 0.7 gm of pyruvate in 1 liter of deionized water. Adjust the pH to 8.0. Add 1500 U of aspartate transaminase (AST) and mix well.

Reaction Cocktail B
Malachite Green 0.0125%

Dissolve 12.5 gm of malachite green carbinol base in 100 ml of deionized water.

ALT Standards
ALT 0, 10, 15, 25, 50, 100, 200 U/L

ALT standards are prepared by dissolving alanine aminotransferase in deionized water to give the desired activity level (U/L).

Protocol

1. Prepare the reaction mixture before each analysis. Mix cocktail A and cocktail B at the ratio of 10:1. To each micro-cuvette pipet 1 ml of the reaction mixture.

2. To each micro-cuvette pipet 100 ul of sample, ALT standards, or reaction mixture (for blank).

3. Read the absorption at 617 nm (referenced to the blank) at 30 second intervals for a period of 5 minutes.

4. Prepare a standard curve for ALT by plotting the rates of decreasing absorption at 617 nm vs. ALT activity (i.e., U/L).

5. The ALT activity in the sample is determined by using the standard curve.

Other embodiments are within the following claims.

We claim:

1. Method for determining the presence of an aminotransferase ($AT_1$), other than aspartate aminotransferase (AST), in a biological sample, comprising the steps of;
   reacting said sample with:
   an amino donor substrate for said $AT_1$;
   a second aminotransferase ($AT_2$), different from $AT_1$, in excess as to not limit the rate of the $AT_1$ to form beta-keto acid;
   an amino acceptor substrate for said $AT_1$, nonreactive with said $AT_2$;
   cysteine sulfinic acid (CSA) in excess as to not limit the rate of reaction of $AT_2$; and
   an indicator for the presence of sulfite ions, nonreactive with said $AT_1$, said $AT_2$, said CSA, said amino donor substrate, and said amino acceptor substrate;
   under conditions in which the concentration of said $AT_1$ in the sample can be determined by the amount of the indicator which forms a detectable signal.

2. The method of claim 1, wherein said aminotransferase ($AT_1$) is L-alanine aminotransferase (ALT).

3. The method of claim 1, wherein the indicator exhibits a detectable spectral change during the reaction.

4. The method of claim 3, wherein the spectral change is detected by an instrument.

5. The method of claim 3, wherein the spectral change is detected visually as a colorimetric change.

6. The method of claim 1, wherein the indicator is a triarylmethine dye.

7. The method of claim 6, wherein the dye is selected from the group consisting of malachite green, methyl green, and guinea green B.

8. The method of claim 1, wherein the indicator contains a contrast dye.

9. The method of claim 8, wherein the contrast dye is selected from the group consisting of rhodamine B, ethyl violet, acid fuchsin, basic fuchsin, pararosaniline chloride, pararosaniline acetate, and aurin sodium salt.

10. The method of claim 1, wherein the aminotransferase reaction conditions include a buffered aqueous medium having pH in the range of about 3.0 to 10.0.

11. The method of claim 1, wherein the presence of the aminotransferase ($AT_1$) is indicative of a disease condition.

12. The method of claim 11, wherein the disease is periodontal disease and the sample comprises crevicular fluid.

13. The method of claim 11, wherein the sample comprises sera.

14. Assay kit for determining the presence of an aminotransferase ($AT_1$), other than aspartate aminotransferase (AST), in a biological sample, said kit comprising at least three containers comprising one or more of the following components;
   an aliquot of an amino donor substrate for $AT_1$;
   an aliquot of a second aminotransferase ($AT_2$), different from $AT_1$;
   an aliquot of cysteine sulfinic acid (CSA);

an aliquot of an amino acceptor substrate for $AT_1$, nonreactive with said $AT_2$; and an aliquot of an indicator for the presence of sulfite ions, nonreactive with said $AT_1$, said $AT_2$, said CSA, said amino donor substrate, and said amino acceptor substrate.

15. The kit of claim 14, wherein the aminotransferase ($AT_1$) is L-alanine aminotransferase (ALT) and the biological sample is crevicular fluid.

16. The kit of claim 14, wherein the amino acid donor substrate is glutamate and the amino acid acceptor substrate is pyruvate.

17. The kit of claim 14, wherein $AT_2$ is aspartate aminotransferase (AST).

18. The kit of claim 14, wherein crevicular fluid sampling papers are included.

19. The kit of claim 14, wherein the indicator is a triarylmethine dye selected from the group consisting of malachite green, methyl green, and guinea green B.

20. The kit of claim 14, wherein the indicator contains a contrast dye which is selected from the group consisting of rhodamine B, ethyl violet, acid fuchsin, basic fuchsin, pararosaniline chloride, pararosaniline acetate, and aurin sodium salt.

21. The kit of claim 17, wherein the amino donor substrate and AST are provided in separate containers.

22. The kit of claim 17, wherein the amino donor substrate and AST are provided in the same container.

23. The kit of claims 21 or 22, wherein the amino donor substrate is glutamate.

24. The kit of claim 14, wherein the kit contains a multiwell tray.

25. The kit of claim 14, wherein an aliquot of an indicator dye as said indicator, an aliquot of a contrast dye and an aliquot of cysteine sulfinic acid (CSA) are coated onto wells of a multiwell tray.

26. The kit of claim 14, wherein an aliquot of an indicator dye as said indicator, an aliquot of a contrast dye and an aliquot of cysteine sulfinic acid (CSA) are coated onto paper.

27. The kit of claim 14, wherein an aliquot of an indicator dye as said indicator, an aliquot of a contrast dye and an aliquot of cysteine sulfinic acid (CSA) are provided in a sugar-based pellet.

28. The kit of claim 14, wherein an aliquot of an indicator dye as said indicator, an aliquot of a contrast dye and an aliquot of cysteine sulfinic acid (CSA) are provided in a powder form.

* * * * *